(12) United States Patent
LeBeau

(10) Patent No.: US 10,070,938 B2
(45) Date of Patent: Sep. 11, 2018

(54) STABILIZATION DEVICE AND METHOD FOR SURGICAL LOCALIZATION WIRE

(71) Applicant: David LeBeau, Redlands, CA (US)

(72) Inventor: David LeBeau, Redlands, CA (US)

( * ) Notice: Subject to any disclaimer, the term of this patent is extended or adjusted under 35 U.S.C. 154(b) by 141 days.

(21) Appl. No.: 15/161,091

(22) Filed: May 20, 2016

(65) Prior Publication Data
US 2017/0333154 A1    Nov. 23, 2017

(51) Int. Cl.
*A61B 90/00* (2016.01)
*A61B 17/00* (2006.01)

(52) U.S. Cl.
CPC .... *A61B 90/39* (2016.02); *A61B 2017/00951* (2013.01); *A61B 2090/3991* (2016.02)

(58) Field of Classification Search
CPC .......... A61B 90/39; A61B 2017/00951; A61B 2090/3991
USPC .......................... 128/897–899; 604/174, 178
See application file for complete search history.

(56) References Cited

U.S. PATENT DOCUMENTS

| 4,161,177 A | 7/1979 | Fuchs | |
|---|---|---|---|
| 4,397,647 A * | 8/1983 | Gordon | A61M 25/02 128/DIG. 26 |
| 4,592,356 A | 6/1986 | Gutierrez | |
| 4,774,948 A | 10/1988 | Markham | |
| 5,127,916 A * | 7/1992 | Spencer | A61B 90/39 606/185 |
| 5,147,322 A * | 9/1992 | Bowen | A61M 25/02 128/DIG. 26 |
| 6,270,464 B1 * | 8/2001 | Fulton, III | A61B 90/39 600/562 |
| 6,336,904 B1 * | 1/2002 | Nikolchev | A61B 5/0084 600/562 |
| 7,815,613 B2 | 10/2010 | Raulerson et al. | |
| D629,513 S | 12/2010 | Bierman et al. | |
| 8,663,266 B1 | 3/2014 | Obsuth | |
| D703,317 S | 4/2014 | Kinsey | |
| D715,929 S | 10/2014 | Khalaj | |
| D733,873 S | 7/2015 | Appelbaum et al. | |
| 2002/0099264 A1 * | 7/2002 | Fontenot | A61B 90/17 600/130 |

(Continued)

OTHER PUBLICATIONS

Beekley Medical, "Cradles® Needle Localization Wire Protectors", (2013) http://web.archive.org/web/20140723081054/http://beekley.com/pdf/Beekley-Medical-Catalog-2013.pdf, in 1 page.

*Primary Examiner* — Navin Natnithithadha
*Assistant Examiner* — Sunita Reddy
(74) *Attorney, Agent, or Firm* — Procopio, Cory, Hargreaves & Savitch LLP

(57) ABSTRACT

A wire stabilization device and method for stabilizing a localization wire during a tissue diagnostic procedure are disclosed. The wire stabilization device includes a device body and a device base. The device body is joined to the device base. The device body includes a base portion, a cover portion, a cover hinge, and a gripping feature. The cover hinge connects the base portion to the cover portion and allows the cover portion to rotate between open and closed positions. The gripping feature holds the localization wire between the base portion and the cover portion. The device base attaches to a patient's skin to stabilize the device body while the localization wire is held between the base portion and the cover portion.

7 Claims, 15 Drawing Sheets

(56) References Cited

U.S. PATENT DOCUMENTS

| | | | | |
|---|---|---|---|---|
| 2005/0165299 A1* | 7/2005 | Kressy | ............... | A61B 90/10 |
| | | | | 600/411 |
| 2007/0265572 A1* | 11/2007 | Smith | ............... | A61M 25/02 |
| | | | | 604/174 |
| 2008/0027266 A1* | 1/2008 | Lebovic | ............... | A61N 5/1027 |
| | | | | 600/3 |
| 2009/0048537 A1 | 2/2009 | Lydon et al. | | |
| 2011/0166529 A1* | 7/2011 | LeLievre | ............... | A61M 25/02 |
| | | | | 604/180 |
| 2012/0109069 A1* | 5/2012 | Dickert | ............... | A61M 25/02 |
| | | | | 604/178 |
| 2013/0289359 A1 | 10/2013 | Ritter et al. | | |
| 2017/0340891 A1* | 11/2017 | Boggs | ............... | A61N 1/37241 |

* cited by examiner

STABILIZATION DEVICE AND METHOD FOR SURGICAL LOCALIZATION WIRE

BACKGROUND

1. Field of the Invention

This invention relates generally to wire stabilization and is directed toward a stabilization device for surgical localization wire.

2. Related Art

Screening or diagnostic procedures are used to identify the location of a suspicious growth of tissue or abnormality, such as cysts, calcifications, and tumors, in living tissue. For example, a mammography is a screening procedure used to identify a suspicious growth within the human breast tissue. When a suspicious growth of tissue is identified, the location of the growth must be identified to direct a surgeon to the location of the growth for biopsy or removal of the growth. Prior to surgery, a localization wire is inserted into the living tissue to identify the location of the growth. In the waiting period between insertion of the localization wire and the surgery the localization wire may migrate, which may result in the removal of tissue at a location different than that of the growth. Gauze, medical tape, medical dressings, and disposable cups may be used to cover the wire during the waiting period. However, these materials may not prevent migration of the localization wire.

SUMMARY

A wire stabilization device for securing a localization wire to a patient's skin is disclosed herein. In embodiments, the wire stabilization device includes a device body and a device base. The device body has a reception end for receiving the localization wire adjacent to the location that the localization wire exits the patient's skin and a device distal end opposite the reception end. The device body includes a base portion, a cover hinge, a cover portion, a gripping feature, and a cover coupling mechanism. The cover hinge adjoins the base portion on a first side of the device body. The cover portion adjoins the cover hinge on the first side. The cover portion rotates about the cover hinge between a closed position and an open position. The cover portion is adjacent to the base portion at a second side of the device body opposite the first side when in the closed position. The gripping feature holds the localization wire between the base portion and the cover portion when the cover portion is in the closed position. The cover coupling mechanism holds the cover portion in the closed position.

The device base attaches to the patient's skin. The device base includes an adhesive portion body and a device joining portion. The adhesive portion body is shaped to include an adhesive portion slot. The device joining portion joins the base portion to the adhesive portion body with the reception end located adjacent the adhesive portion slot.

A method for stabilizing a localization wire during a medical tissue diagnostic procedure is also disclosed. In embodiments, the method includes affixing a device base of a wire stabilization device to a patient's skin with the localization wire extending out of the patient's skin within an adhesive portion slot of the device base and adjacent to a reception end of a device body of the wire stabilization device. The method also includes bending the localization wire at a location adjacent to the reception end. The method further includes closing the device body by rotating a cover portion about a cover hinge from an open position to a closed position adjacent to a base portion that is joined to the device base with a portion of the localization wire extending therebetween and held by a gripping feature of the wire stabilization device located between the base portion and the cover portion.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Figure 1:
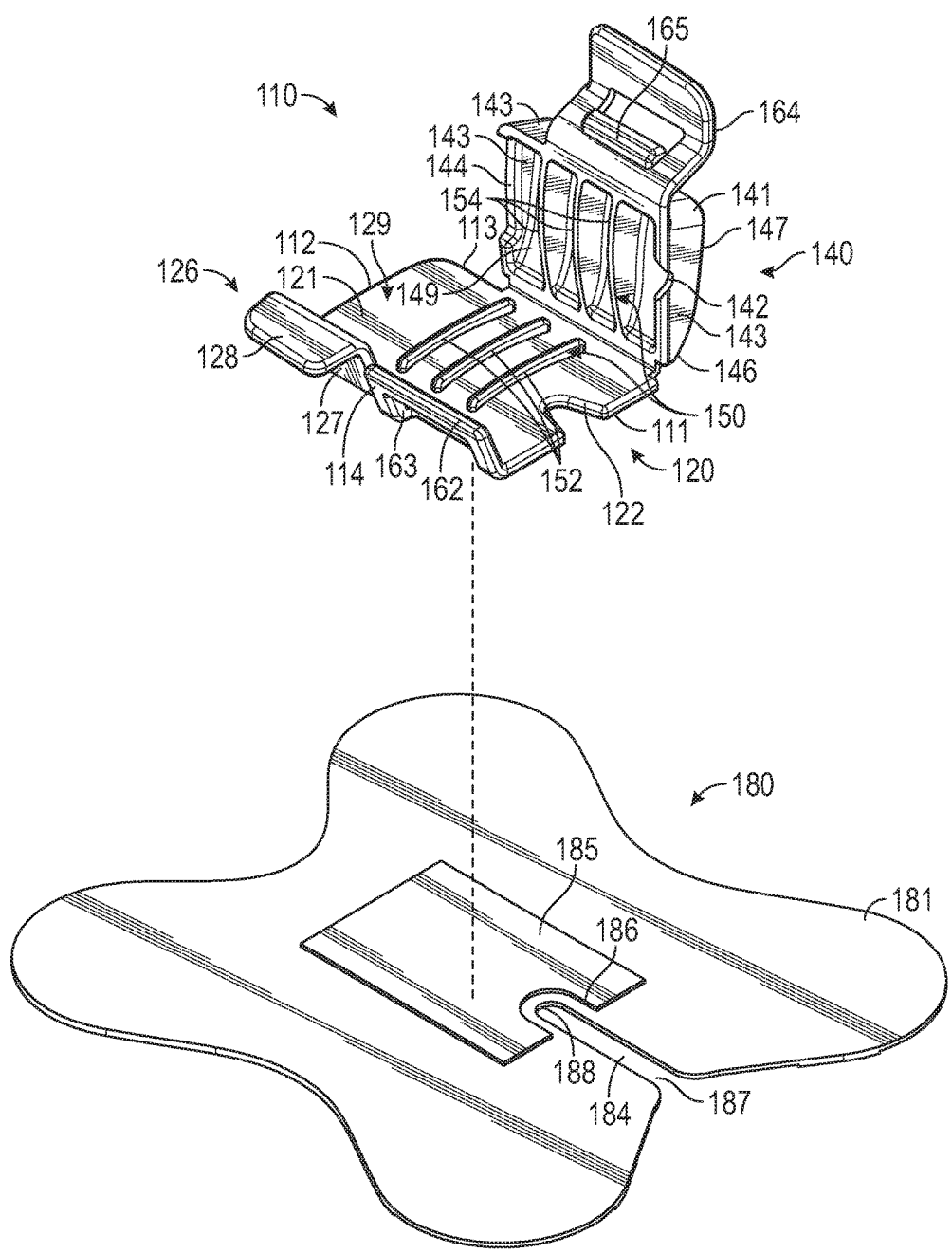
FIG. 1 is an exploded view of a first embodiment of a wire stabilization device.

Certain embodiments as disclosed herein provide for a device and method for securing an external end or body exiting portion of a localization wire extending into a patient's body for surgical site identification purposes to the patient's skin immediately adjacent the wire entrance wound for the time period between wire placement and actual surgery, reducing the risk of the wire migrating prior to surgery.

After reading this description it will become apparent to one skilled in the art how to implement the invention in various alternative embodiments and alternative applications. However, although various embodiments of the present invention will be described herein, it is understood that these embodiments are presented by way of example only, and not limitation.

FIGS. 1-10H illustrate one embodiment of a wire stabilization device 100 for securing the body exiting portion of a localization wire 15 to a patient's skin 10. As best illustrated in FIGS. 1-7, wire stabilization device 100 includes a device body 110 which is designed to grip a body exiting portion of localization wire 15, and a device base 180 which affixes the device body 110 to the patient's skin 10, as described in more detail below.

FIGS. 2 to 9 illustrate one embodiment of the device body 110 in more detail. Device body basically comprises a base portion 120, a cover portion 140 pivotally secured to one side of the base portion via a living hinge 145, a latch mechanism 160 for releasably securing the cover portion 140 over the base portion in the closed condition of FIGS. 3 and 9, and a gripping mechanism 150 including gripping features 152 and 154 protruding from opposing surfaces 121 and 149 of the base portion 120 and cover portion 140, respectively, as described in more detail below.

FIGS. 1 to 9 also illustrate one embodiment of device base 180. As illustrated in FIG. 1, in one embodiment base 180 comprises a first panel or layer 181 of generally butterfly shape and a body joining portion or layer 185 of smaller dimensions than panel 181 adhesively secured to an upper surface of panel or layer 181. Adhesive or body joining layer 185 is secured to the lower surface of base portion 120. In an alternative embodiment, super glue or heat bonding may be used in the manufacturing process to secure panel 181 to the lower surface of plastic device body 110, eliminating layer 185. The panel 181 may have an adhesive backing and may be made of a flexible or pliable material that generally conforms to the shape of the patient's tissue, such as a human breast, to which it is applied during use. Layer 181 may be an adhesive bandage, such as border gauze that includes medical gauze and peripheral tape. Body joining portion or layer 185 may comprise double sided adhesive tape or other bonding means. In one embodiment, the wire stabilization device may be supplied with the device body 110 already joined to the device base 180 during manufacture by superglue or heat bonding, or these parts may be supplied separate from one another in another embodiment, and the device body 110 may be joined to the device base 180 after attachment of the device base to a patient's skin.

Figure 2:
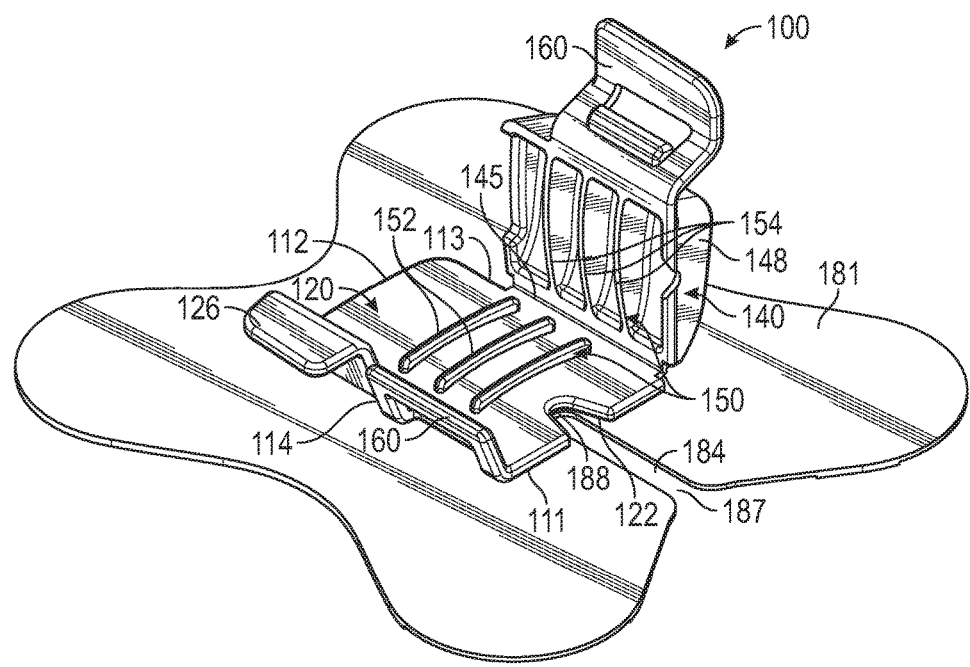
FIG. 2 is a perspective view of the wire stabilization device of FIG. 1 in a partially open condition.
Figure 6:
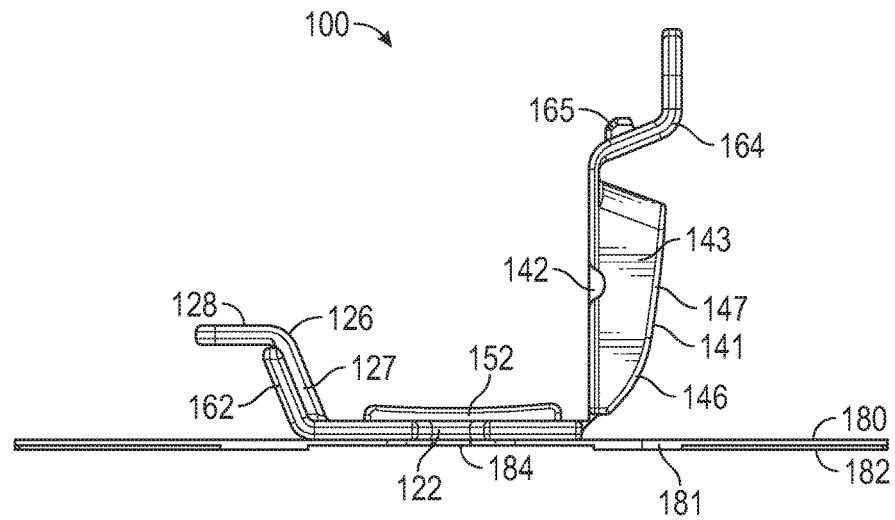
FIG. 6 is a front view of the wire stabilization device in the open condition of FIG. 2.
Figure 7:
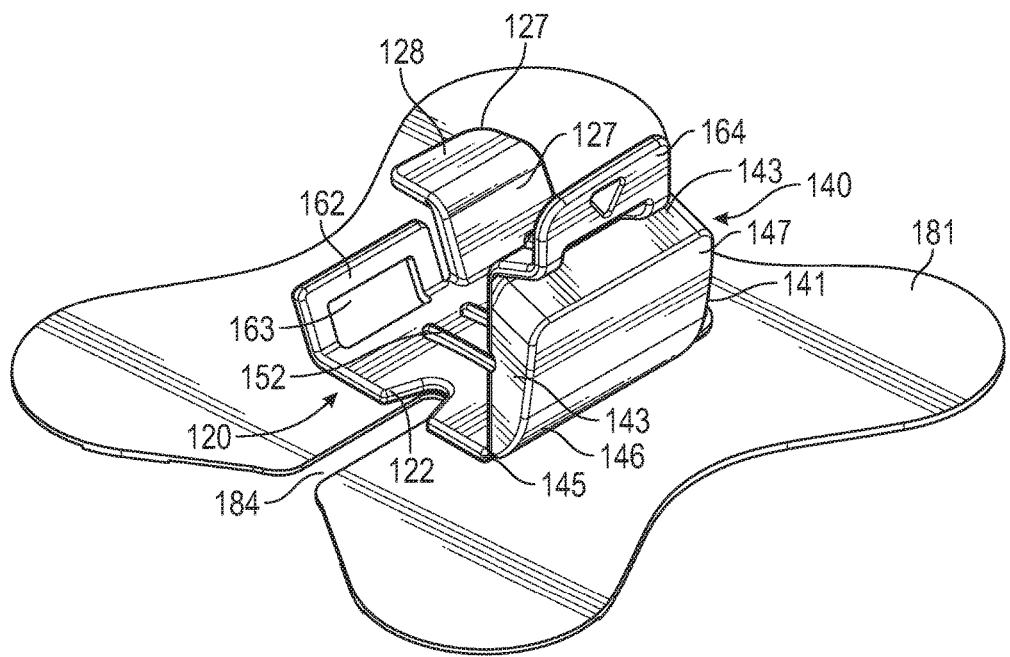
FIG. 7 is a perspective view of the wire stabilization device in the open condition of FIG. 2 viewed from an alternate angle.

The first panel or body 181 and the body joining portion 185 have aligned slots 184 and 186 extending from one edge and positioned for alignment with a corresponding recess or slot 122 in the corresponding edge of base portion 120 when the joining portion 185 is secured to the lower surface of base portion 120, as seen in FIGS. 2 to 7 and described in more detail below. Slot 184 has an outer open end 187 and an inner end 188, as seen in FIGS. 1 and 2. First panel or body 181 may be of different peripheral shapes such as rectangular in alternative embodiments. Referring to FIGS. 6 and 100, the device base 180 may also include a lower layer of skin adhesive 183 on the bottom or lower surface of base panel 181, and a peel away cover layer 182 over the skin adhesive which protects the skin adhesive 183 until the wire stabilization device 100 is to be secured to the patient. The skin adhesive cover 182 may be peeled away from the skin adhesive layer 183 prior to securing the wire stabilization device 100 to the patient, as described in more detail below.

Figure 3:
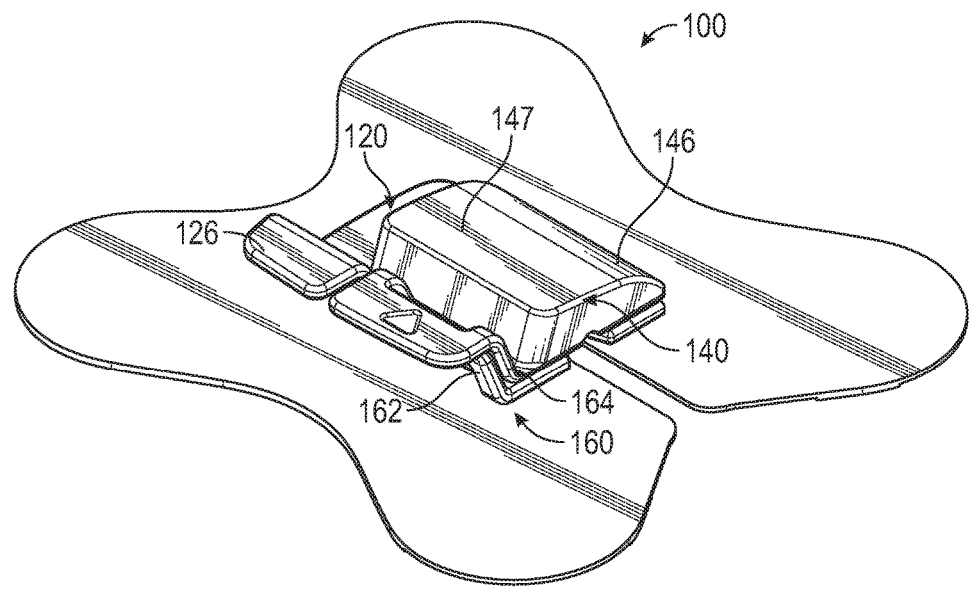
FIG. 3 is a perspective view of the wire stabilization device of FIG. 1 in the closed condition.
Figure 4:
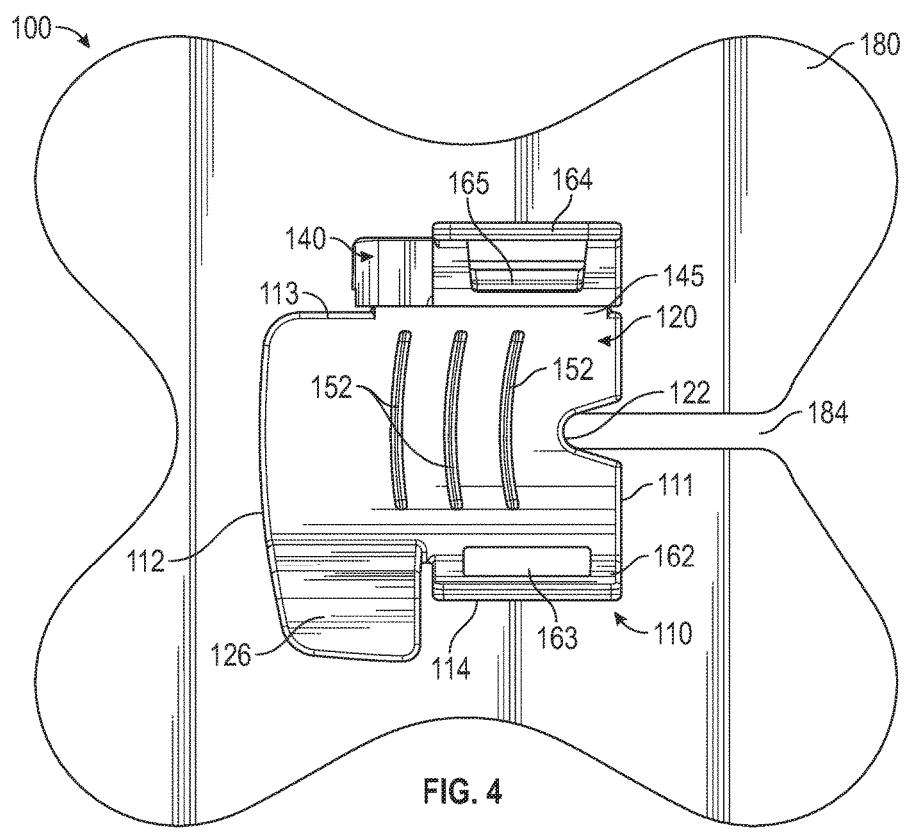
FIG. 4 is a top view of the wire stabilization device of FIG. 1.
Figure 5:
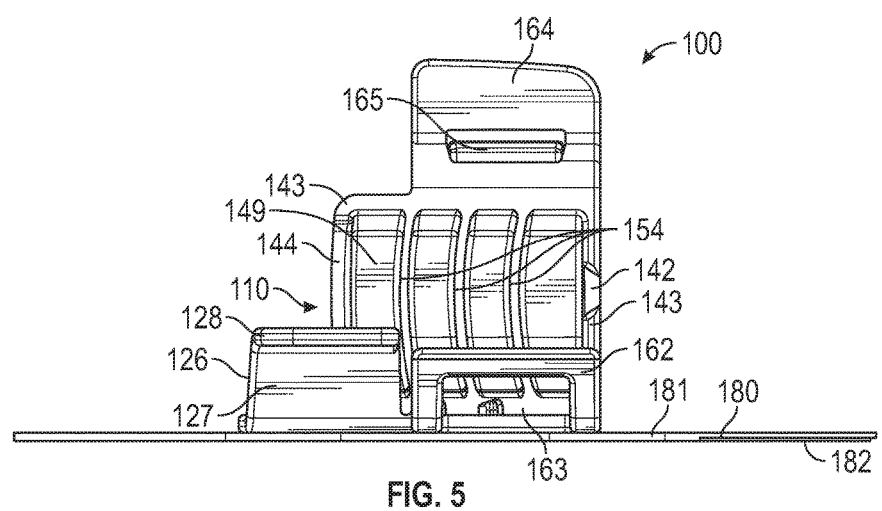
FIG. 5 is a side elevation view of the wire stabilization device in the open condition of FIG. 2.
Figure 8:
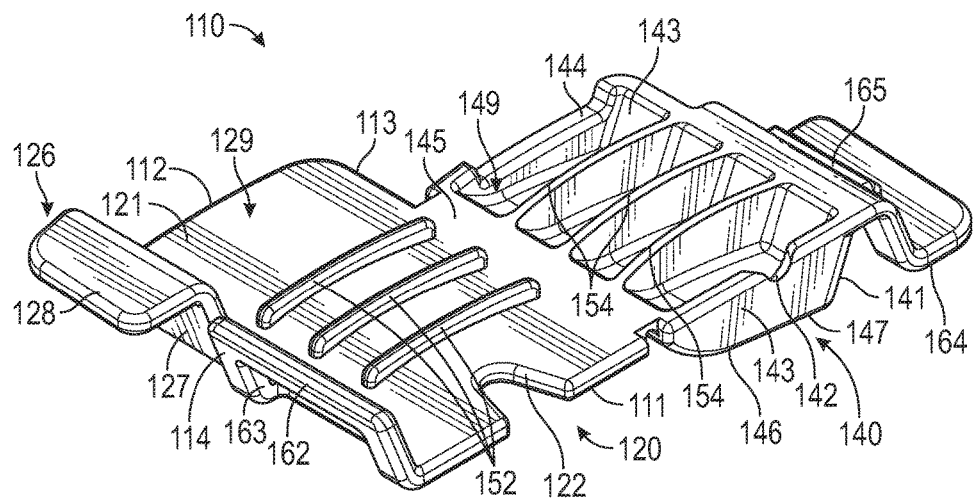
FIG. 8 is a perspective view of the device body in a fully open condition.
Figure 9:
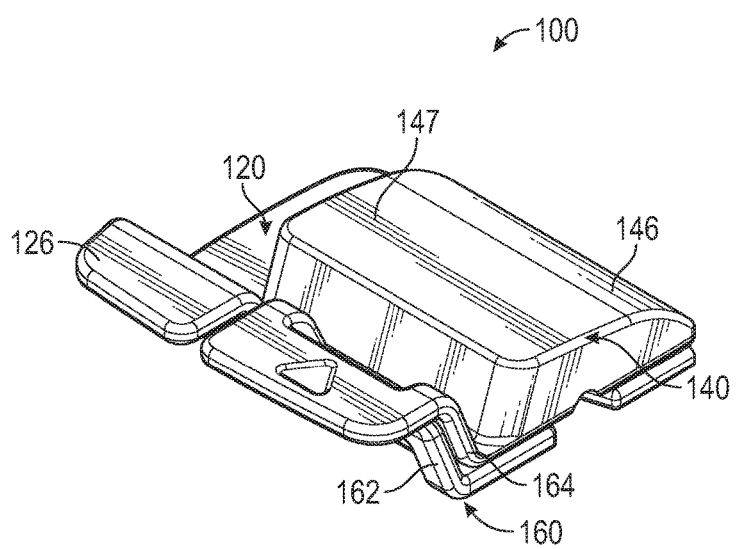
FIG. 9 is a perspective view of the device body in the closed condition of FIG. 3.

FIG. 8 illustrates the device body 110 in a fully open position and FIGS. 3 and 9 illustrate the device body 110 in a closed and latched position. Referring to FIGS. 8 and 9, the device body 110 includes a reception end 111 which includes base slot or indent 122 that is configured to receive a localization wire 15 closest to where the body exiting portion of the localization wire exits the patient's skin 10, a device distal end 112 that is opposite the reception end 111 where a distal end portion 17 of wire 15 exits the device body 110 (see FIG. 10E), a first side 113, and a second side 114. The base portion 120 may include a base wall 129 with base slot 122, a tab 126, and a first latch member 162 of latch mechanism 160 extending from the side 114 of base wall 129 opposite to hinge 145. In the embodiment illustrated, base wall may be a flat or substantially flat plate. The base wall 129 may be shaped to include base slot 122 extending into the base wall from the reception end 111 towards the device distal end 112. The base slot 122 may be centered between the first side 113 and the second side 114. An operator may use tab 126 to hold the body portion 120 in place while moving the cover portion 140 to open or close the device body 110. The tab 126 may include an elevation portion 127 extending up from the base wall 129 in the general direction of the cover portion 140 when in a closed position and in the general direction away from the body portion 120. The tab 126 may also include an arm portion 128 extending out from the elevation portion 127 and transverse to the elevation portion 127, such as in the direction away from the second side 114.

Cover portion 140 may include a cover body 141, cover walls 143, a cover entrance slot 142, and a cover exit slot 144. The cover body 141 may be connected to the base wall 129 by the cover hinge 145. The cover body 141 may have an outer convex portion 146 that extends from the cover hinge 145 and a plate portion 147 that is flatter and extends from the concave portion 146 in the direction opposite the cover hinge 145. The cover body 141 may include a cover portion surface 149 that forms an interior surface of the cover body 141. The cover portion surface 149 faces the base portion 120 when the device body 110 is in the closed condition of FIG. 9 with the cover portion 140 latched to the base portion 120, as described in more detail below.

The cover walls 143 extend from opposites sides of portion 147 of cover body 141 and may form a hollow interior together with concave portion 146. The cover walls 143 may extend toward the base surface 121 when the device body 110 is in a closed condition. The cover walls 143 may have outer edges shaped to form the cover entrance slot 142 at the reception end 111 and to form the cover exit slot 144 at the device distal end 112. In the closed condition, the cover entrance slot 142 may be aligned with the base slot 122 and cover exit slot 144 may be spaced from the base surface 121 at the device distal end 112 to form a wire exit gap between the base portion surface 121 and the cover walls 143 at the device distal end 112.

Figure 10A:
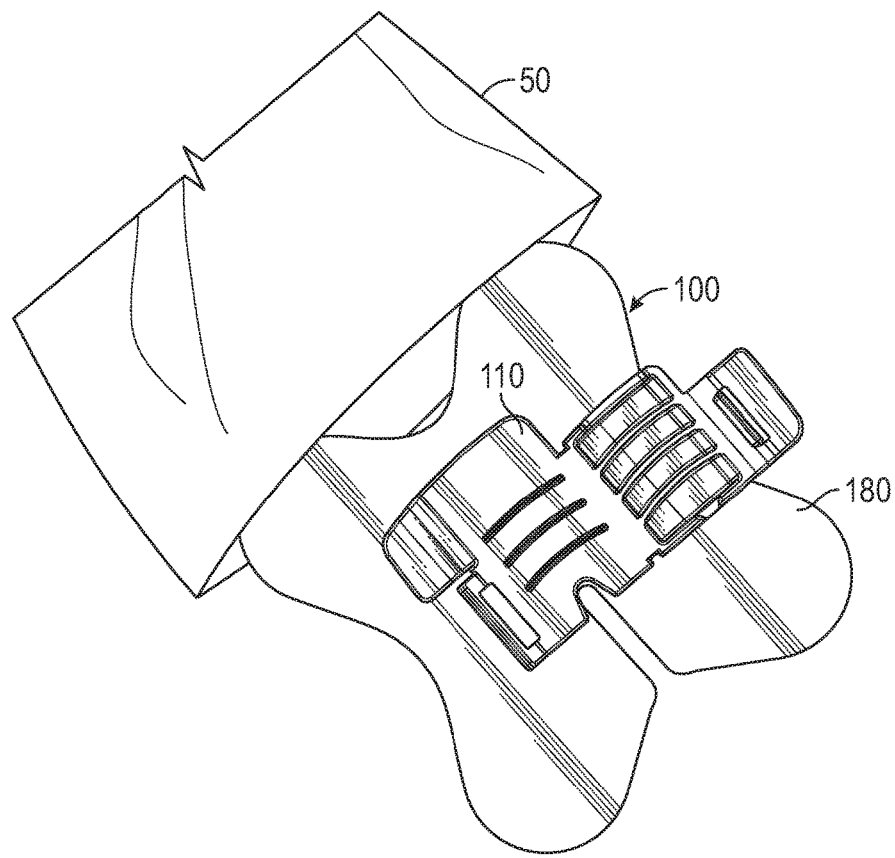
FIGS. 10A-10H are perspective views of the wire stabilization device of FIG. 1 and illustrate an embodiment of the method of use.

Opposing gripping features 152,154 are configured to grip and hold the localization wire 15 between the base portion 120 and the cover portion 140 in the closed condition of device body 110. In the illustrated embodiment, gripping features 152, 154 include, inter alia, spaced protrusions such as ribs or ridges, extending from the inner surface 121 of base portion 120 and inner surface 149 of cover body 141, respectively. The gripping features generally extend transverse to the localization wire 15 when the localization wire extends between the inner surface 121 of base portion 120 and the cover body 141 between the first side 113 and the second side 114, as best illustrated in FIG. 10D. The cover feature or ribs 154 may be offset relative to the base feature or ribs 152, such that each rib 152 extends into a respective space between cover features or ribs 152 when the device body 110 is in the closed condition.

The cover coupling mechanism 160 is a mechanism, such as a fastener, clasp, clip, buckle, pin, or hasp, which couples the base portion 120 to the cover portion 140 in the closed condition to prevent the cover portion 140 from rotating about the cover hinge 145 to an open condition. In the embodiment illustrated, the cover coupling mechanism 160 is located at the first side 113 and opposite the cover hinge 145. The cover coupling mechanism 160 may include a base coupler or first latch member 162 and a cover coupler or second latch member 164. The base coupler 162 may extend from the base portion 120 at the first side 113 and the cover coupler 164 may extend from the cover portion 140 at the first side 113. In the embodiment illustrated, the base coupler 162 includes a coupling or latch slot 163 and the cover coupler 164 includes a coupling protrusion or latch 165 configured for releasable latching or snap engagement through slot 163 when the cover portion is closed over base portion, to hold the cover portion 140 in the closed condition.

Figure 10B:
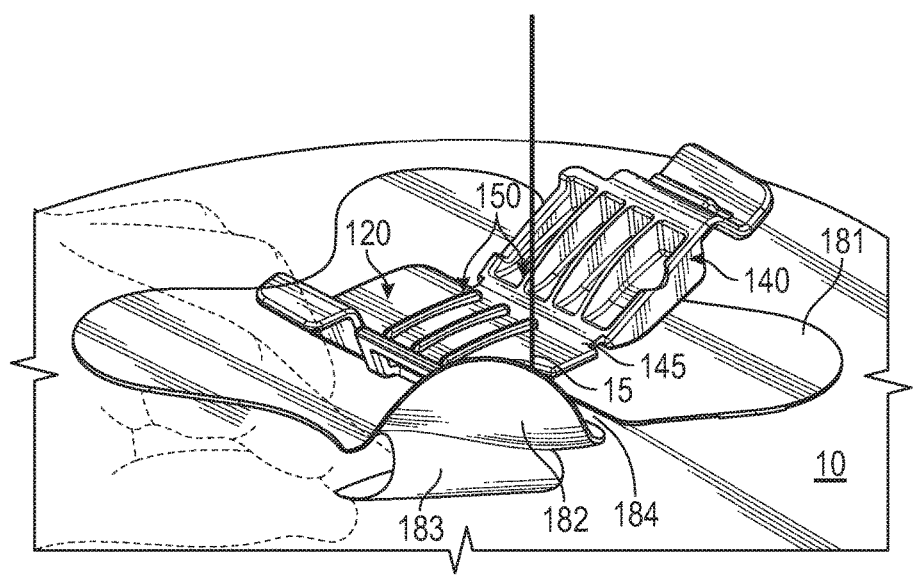
Figure 10C:
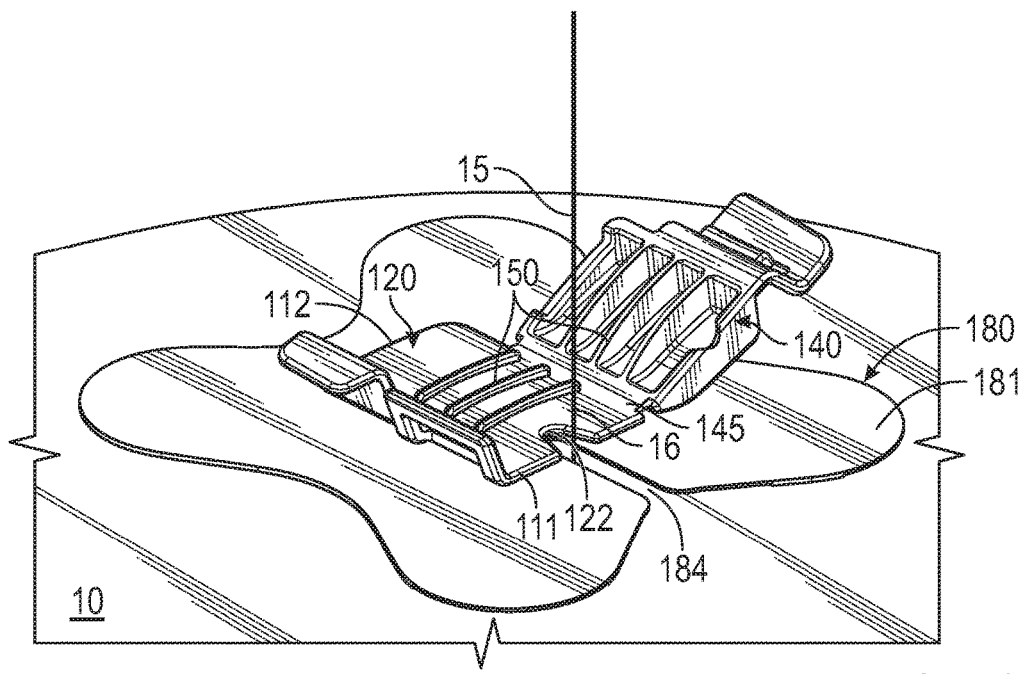
Figure 10D:
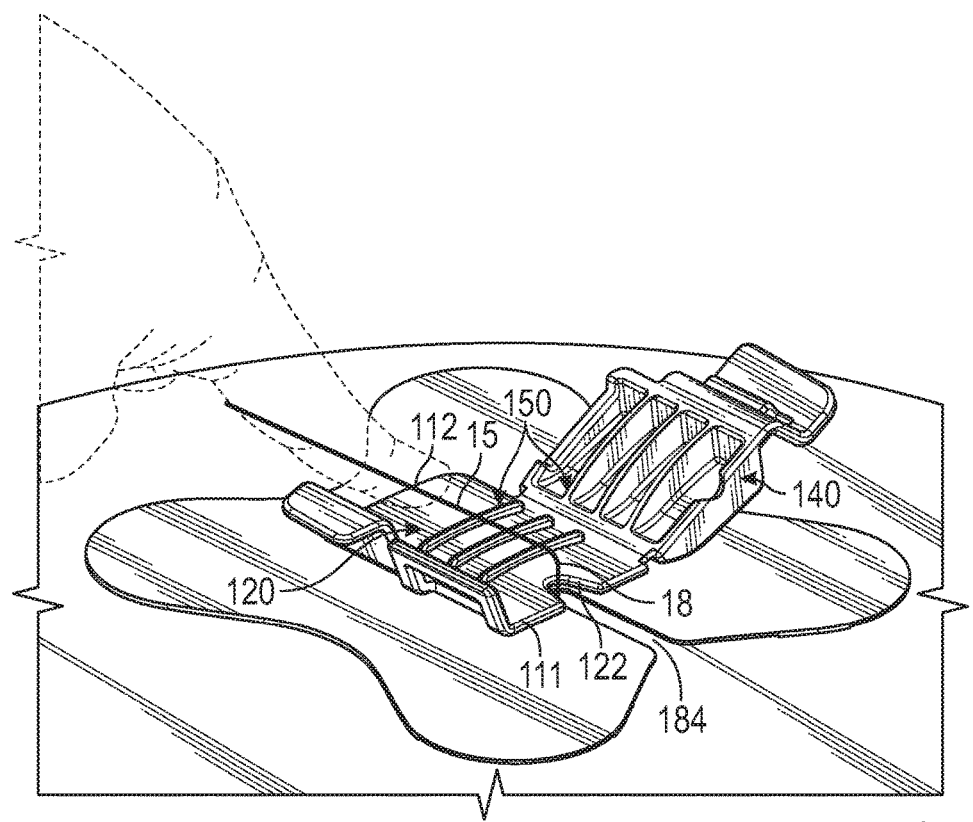
Figure 10E:
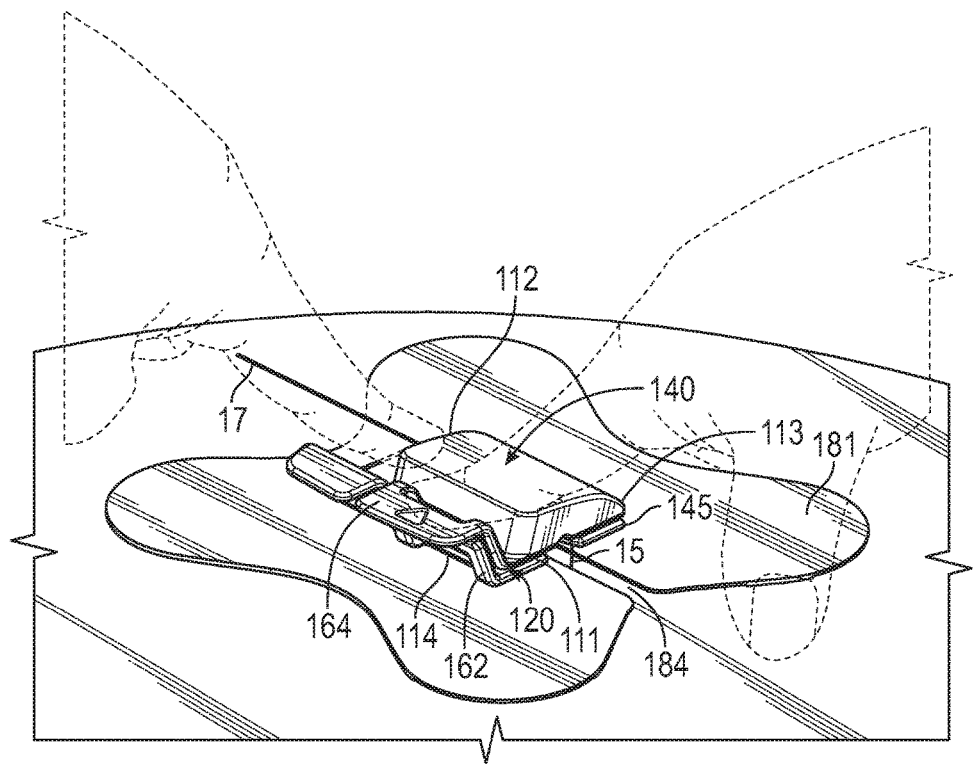
Figure 10F:
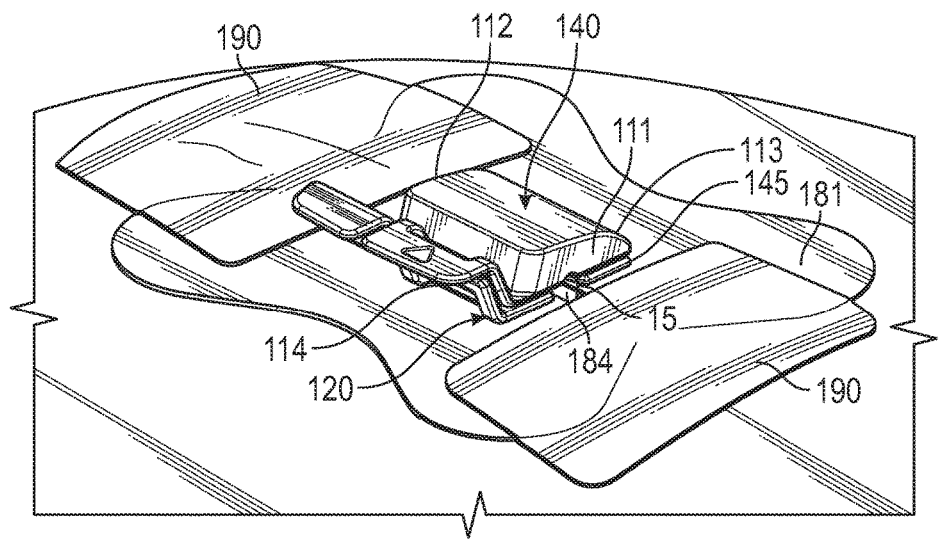
Figure 10G:
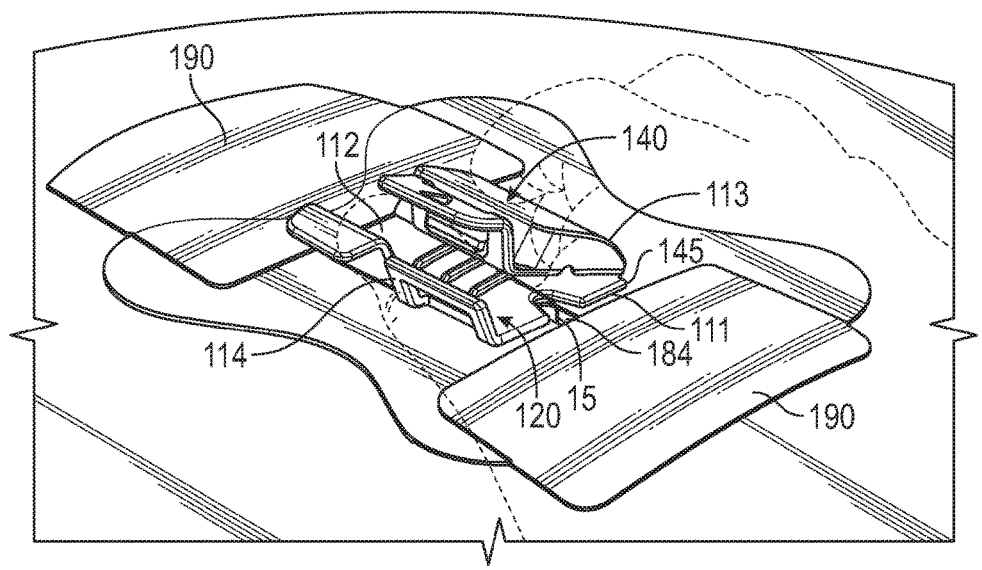
Figure 10H:
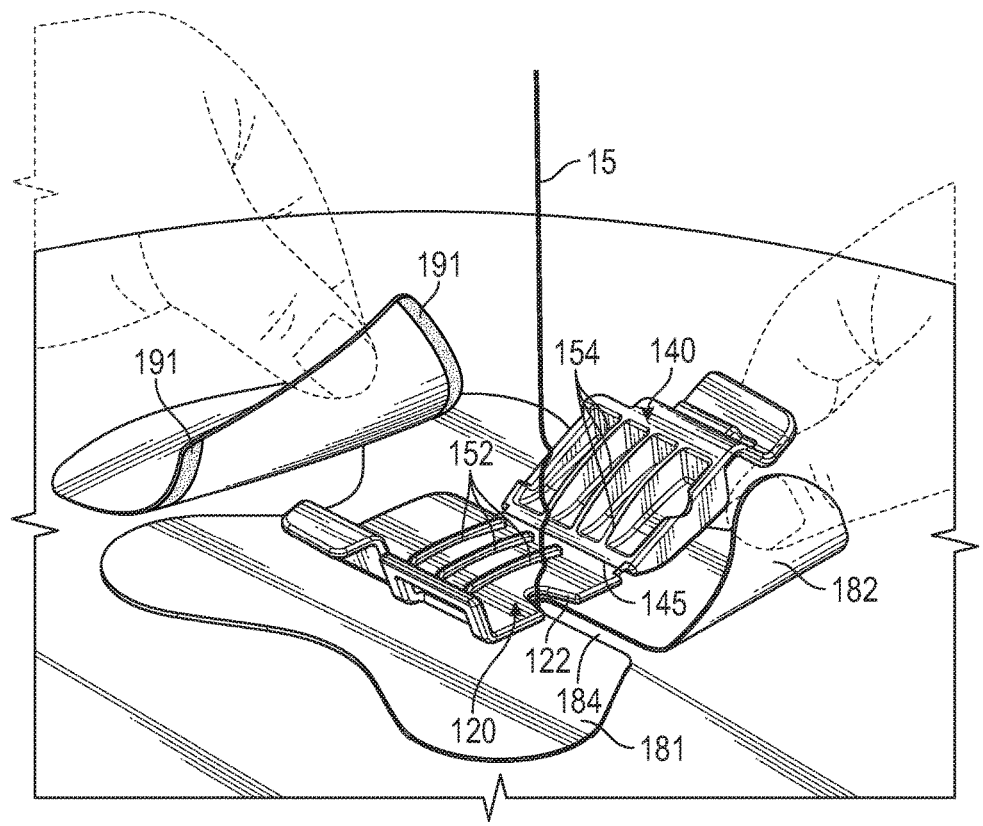
Figure 11:
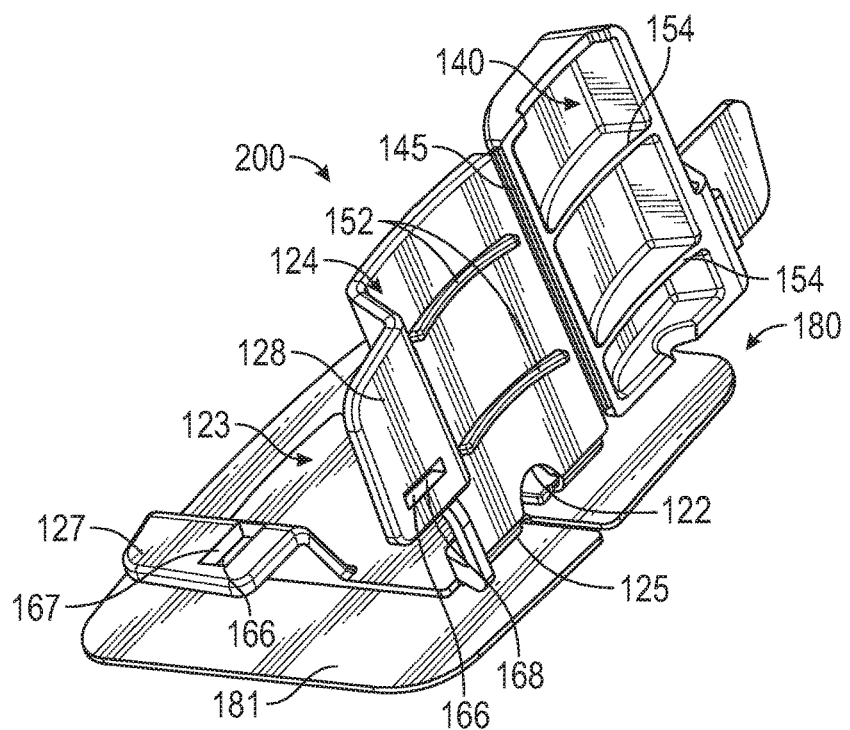
FIG. 11 is a perspective view of an alternate embodiment of the wire stabilization device of FIG. 1 in an open condition.
Figure 12:
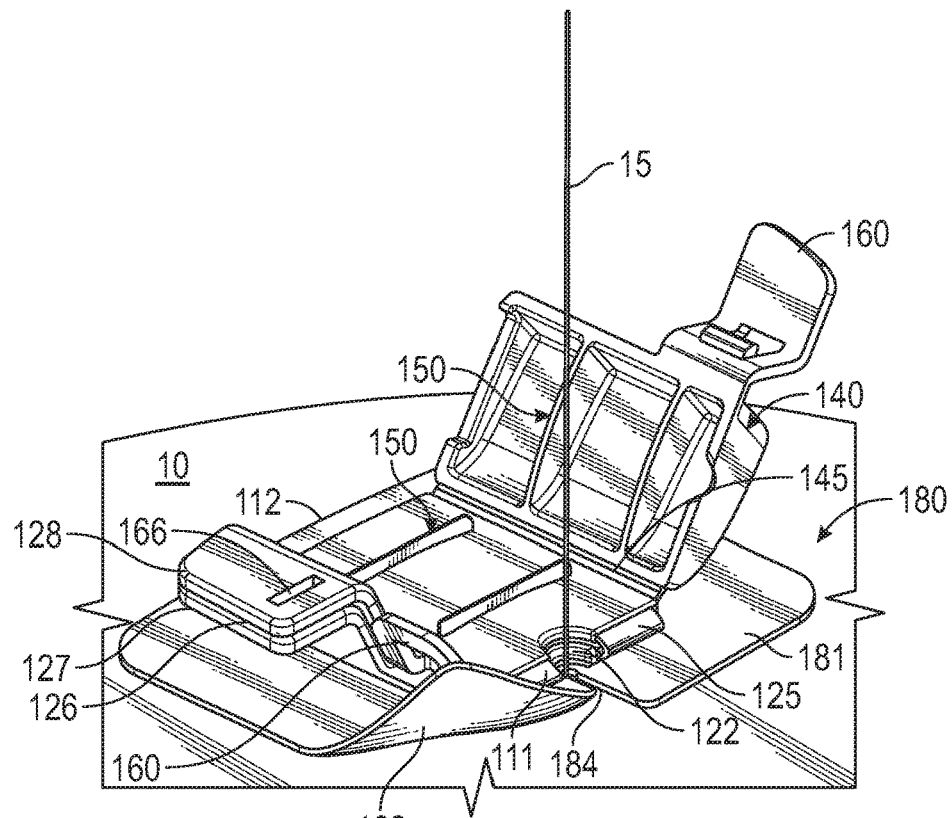
FIG. 12 is a perspective view of the wire stabilization device of FIG. 1 attached to the skin of a patient in an initial partially closed condition.

As illustrated in FIGS. 10F and 10G, the wire stabilization device 100 may include one or more cover strips or adhesive bandages 190 used to further secure the wire stabilization device 100 to the patient's skin 10. In the embodiment illustrated, a cover strip, bandage or tape 190 partially covers the device base 180 adjacent the reception end 111, and a similar cover strip 190 partially covers the device base 180 adjacent the device distal end 112. Cover strips have adhesive covering all or part of their inner surfaces. As illustrated in FIG. 10H, adhesive strips 191 may be provided on the inner surface of the cover strip 190 adjacent each side edge of the cover strip with no adhesive on the part of strip 190 which covers the extending end portion of wire 15.

The wire stabilization device 100 is used during medical tissue screening procedures, such as a mammography, to stabilize the localization wire 15 and restrict migration of the localization wire 15 prior to surgery. The screening procedure may include the steps of scanning the living tissue for a suspicious growth, inserting the localization wire 15 into the living tissue to identify the location of a selection of tissue of the suspicious growth, stabilizing the location wire with the wire stabilization device 100 while awaiting surgery, removing the wire stabilization device 100 before surgery, and removing the selection of tissue from the living tissue identified by the localization wire.

Figure 25:
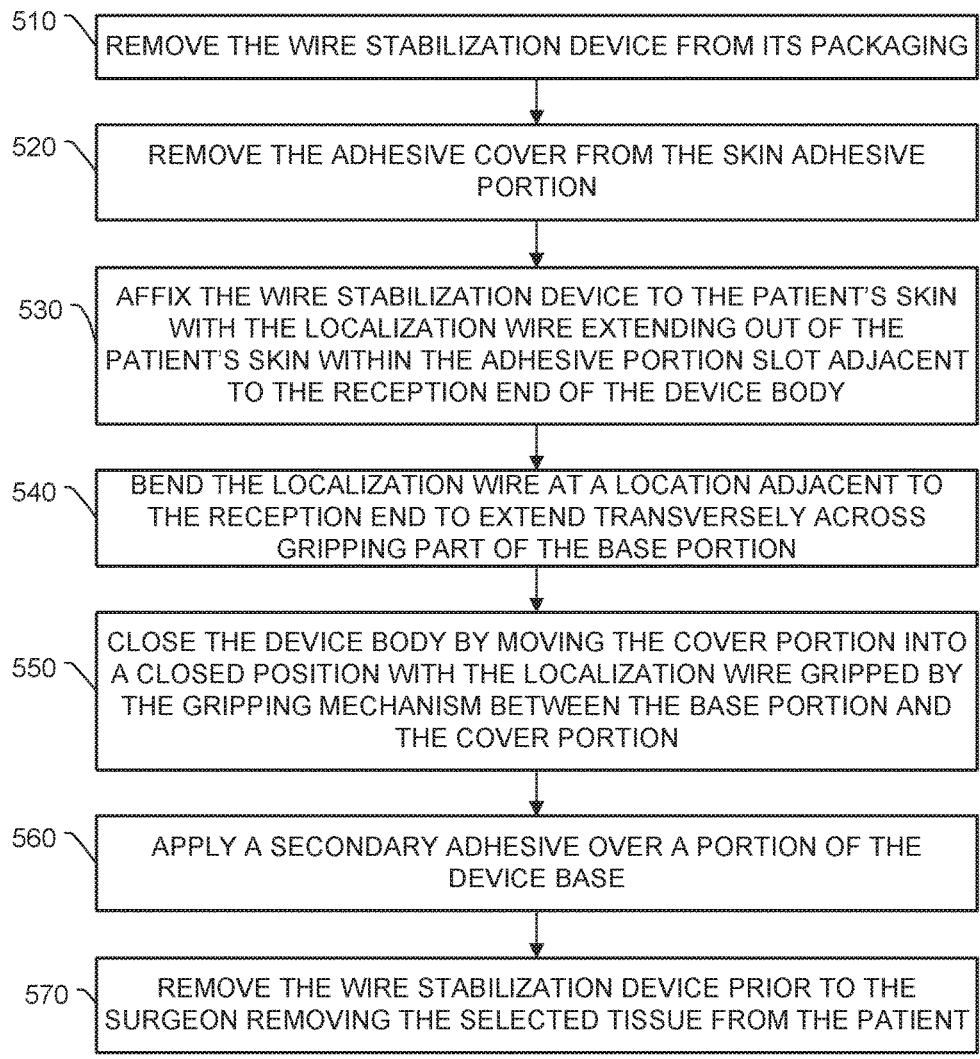
FIG. 25 is a flowchart of one embodiment of a method for stabilizing a localization wire during a medical tissue screening procedure with the wire stabilization device of any of the embodiments of FIGS. 1-24.

FIG. 25 is a flowchart of a method for stabilizing a localization wire 15 during a medical tissue screening procedure with the wire stabilization device 100 of FIGS. 1 to 9. FIGS. 10A-10H illustrate the steps of the method of FIG. 25. Referring to FIG. 10A, the method may include removing the wire stabilization device 100 from its packaging 50 at step 510. The packaging 50 may be a sterile package. The device body 110 may be in an open or closed condition when the wire stabilization device 100 is removed from the packaging 50.

Referring to FIG. 10B, the method may also include removing the adhesive cover layer 183 from the skin adhesive 182 at step 520. The method includes affixing the wire stabilization device 100 to the patient's skin 10 with the localization wire 15 extending out of the patient's skin 10 within the adhesive portion slot 184 adjacent to the reception end 111 of the device body 110 at step 530, as illustrated in FIG. 10C.

Referring to FIG. 10D, the localization wire 15 is bent at a location adjacent to the reception end 111 at step 540 of FIG. 25. The localization wire 15 may be bent to run parallel to the patient's skin 10 and transversely across ribs 152 of gripping mechanism 150 with a bend 18 formed in the localization wire 15 adjacent to the reception end 111, as illustrated in FIG. 10D.

Referring to FIG. 10E, step 550 of the method comprises closing the device body 110 by moving the cover portion 140 into a closed position with the localization wire 15 gripped by the opposing ribs 152, 154 between the base portion 120 and the cover portion 140. When the ribs 152, 154 are offset slightly, the gripping mechanism 150 may bend the localization wire 15 between adjacent interleaved ribs 152, 154 which may improve grip of the gripping mechanism 150. Step 550 may include closing the cover coupling mechanism 160, such as by engaging latch members 162 and 164 as seen in FIG. 10E, to prevent the device body 110 from inadvertently opening.

Referring to FIG. 10F, the method may also include applying adhesive tape 190 over exposed portions of the device base 180 adjacent the entry and exit ends of the body 110 at step 560. Step 560 may include applying a first piece of adhesive tape 190 over the slot 184 adjacent bend 118 in wire 15, to hold the wire at the inner end 188 of slot 184, and applying a second piece of adhesive tape over the device distal end and the distal end portion 17 of the localization wire 15 protruding out of the device distal end 112.

Referring to FIGS. 10G and 10H, the method may include removing the wire stabilization device 100 at step 570 prior to surgery in which the surgeon removing the selected tissue located by the wire from the patient. Step 570 may include releasing latch mechanism 160 (FIG. 10G) and then removing both pieces of adhesive tape 190, fully opening the wire stabilization device 100, and bending the localization wire 15 away from the device body 110 as seen in FIG. 10H. The device base 180 is then peeled away from the patient's skin 10 (FIG. 10H). The wire stabilization device 100 may need to be removed in order for the surgeon to reach the selected tissue to remove.

The method illustrated in FIGS. 10A-10H is subject to many variations, including adding, omitting, reordering, or altering steps. Additionally, steps may be performed concurrently. For example, the steps of bending the localization wire 15 at step 540 may be performed before or during closing the device body 110 at step 550.

FIGS. 11-15 illustrate an alternate embodiment of a stabilization device 200. Some parts of the embodiment of FIGS. 11 to 15 are similar or identical to parts of the device of FIGS. 1 to 10H, and like reference numbers are used for like parts as appropriate. In the embodiment illustrated in FIGS. 11-15, the base body includes a first portion 123, a second portion 124, and a base hinge 125. The first portion 123 may have a plate like shape and may be joined to the device base 180 in a similar manner to that described above in connection with the first embodiment. The second portion 124 may be connected to the first portion 123 by the base hinge 125 at the reception end 111 and adjacent the base slot 122. The base slot 122 may extend into both the first portion 123 and the second portion 124. The second portion 124 may rotate from a closed position adjoining the first portion 123 to an open position that is rotated about the base hinge 125 away from the first portion 123. In the embodiment illustrated, the cover hinge 145 connects the second portion 124 to the cover portion 140 and the base features or ribs 152 extend from the second portion 124. The first portion 123, the second portion 124, the base hinge 125, the cover portion 140, and the cover hinge 145 may all be an integral structure or may be separate structures joined at the hinges.

Figure 13:
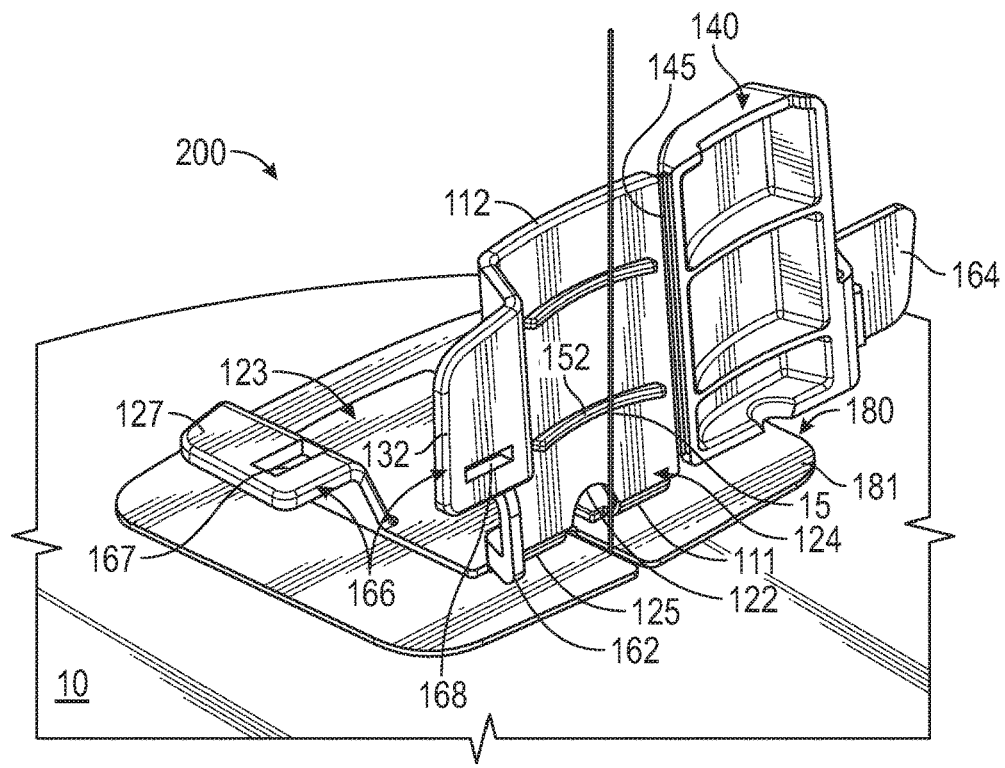
FIG. 13 is a perspective view of the wire stabilization device of FIG. 11 attached to the skin of a patient and in the open condition.
Figure 14:
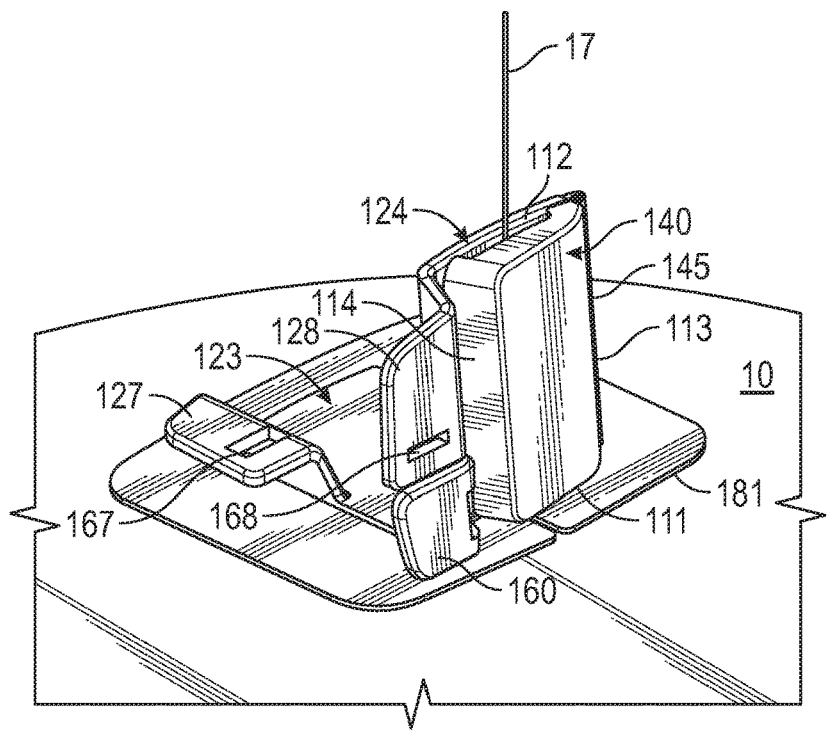
FIG. 14 is a perspective view of the wire stabilization device of FIG. 11 attached to the skin of a patient and grasping the wire in the partially closed condition.

In this embodiment, the second portion 124 may be rotated up into an open position with the localization wire 15 engaging slot 184 in the device base 180 (FIG. 13). The cover portion 140 may then rotate to a closed position to grip the localization wire 15 between the gripping ribs 154 and 152 of the cover portion 140 and second portion 124 of the base (FIG. 14). The second portion 124 may then be rotated back about hinge 125 to the closed position of FIG. 15, bending the localization wire 15.

Figure 15:
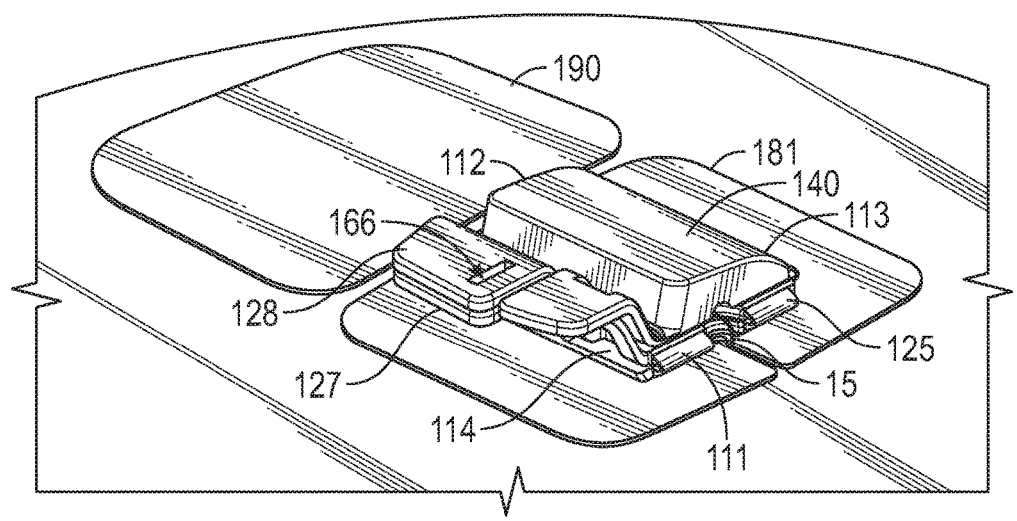
FIG. 15 is a perspective view of the wire stabilization device of FIG. 11 attached to the skin of a patient and grasping the wire in a fully closed condition.

In the embodiment illustrated in FIGS. 11-15, the device body 110 also includes a body coupling mechanism 166 for releasably latching or securing the first portion 123 of the body to the second portion 124. The body coupling mechanism 166 is a mechanism, such as a fastener, clasp, clip, buckle, pin, or hasp, which couples the first portion 123 to the second portion 124 in a closed condition to prevent the second portion 124 from rotating about the base hinge 125 to an open condition. In the embodiment illustrated, the body coupling mechanism 166 includes a first coupler 167 on tab 127 of first portion 123 and a second coupler 168 on tab 128 of second portion 124. In the embodiment illustrated, the first coupler 167 is a slot, while the second coupler 168 is a protrusion or latch member that snaps into the slot of the first coupler 167 to hold the second portion 124 in the closed condition relative to the first coupler 167. In this embodiment, step 550 of FIG. 25 may also include closing the body coupling mechanism 166, such as by clasping or latching the first coupler 167 to the second coupler 168. An adhesive member or piece of adhesive tape 190 is then applied over the protruding portion 17 of localization wire 15 and the base 181, as seen in FIG. 15.

FIGS. 16-19 illustrate another embodiment of a wire stabilization device body 500 which may be secured to a device base 180 in a similar manner to the previous embodiments. In the embodiment illustrated in FIGS. 16-19, the body 500 includes a bulbous portion 133 at the reception end 511 and a thinner base portion 134 adjacent the bulbous portion 133 extending to distal end 512. Slot 122 is replaced by guide groove 522 which extends inward from reception end across bulbous portion 133 toward the base portion 134 to receive a portion of the localization wire 15.

Figure 16:
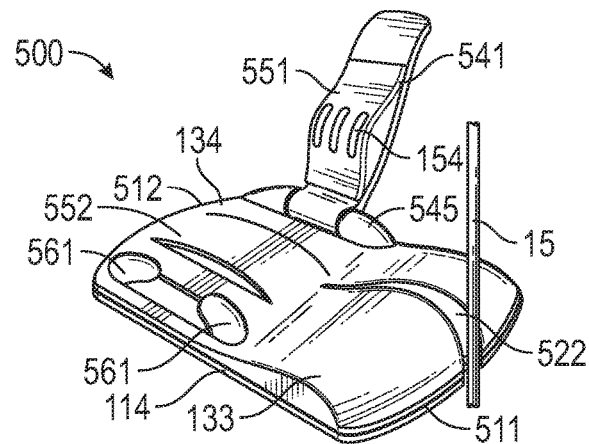
FIG. 16 is a perspective view of an alternate embodiment of the device body of FIGS. 1 and 11 in an open condition.
Figure 17:
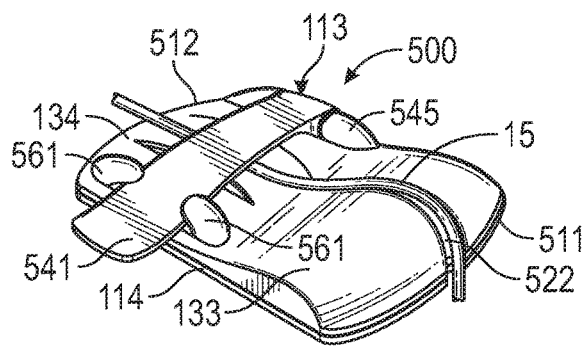
FIG. 17 is a perspective view of the device body of FIG. 16 grasping the wire in a closed condition.
Figure 18:
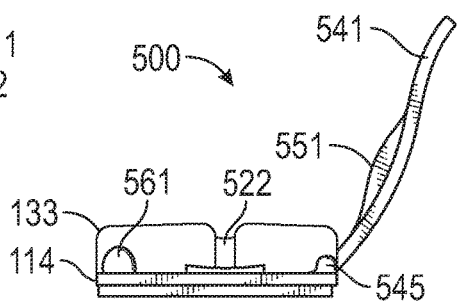
FIG. 18 is a side elevation view of the device body of FIG. 16 in an open condition.
Figure 19:
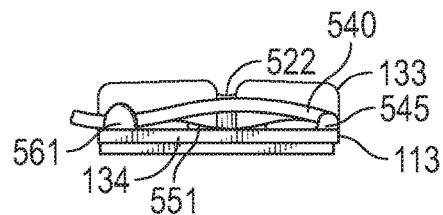
FIG. 19 is a side elevation view of the device body of FIG. 16 in a closed condition.

A narrow cover body 541 is secured to one side 113 of base portion 134 at hinge 545, and is movable between the open position of FIGS. 16 and 19 into the closed position of FIGS. 17 and 19. The cover body 541 and base portion 134 may each include a resilient curved plate or feature 551, 552 respectively that protrude toward the opposing feature when the wire stabilization device body 500 is in a closed condition. The curved plates may be displaced when in a closed condition to apply a spring force to the localization wire 15 held there between. The gripping features may also include ribs 154 located on the base feature 552, the cover feature 551, or both (as shown on the cover feature 551 in FIG. 16).

In the embodiment illustrated in FIGS. 16-19, the cover body 541 is releasably secured in the closed position of FIGS. 17 and 19 by clasps 561 on the opposite side 114 of base portion 134 which engage over the opposite edges of the cover body 541. The method of using the wire stabilization device 500 is similar to that shown in FIG. 25.

Figure 24:
FIG. 24 is a side elevation view of the device body of FIG. 21 in the closed condition.

FIGS. 20-24 illustrate a further embodiment of wire stabilization device body 600. In the embodiment illustrated in FIGS. 20-24, the device body 600 may generally form an elongated oval shape when in an open condition, with a base portion 621 secured to arcuate cover portion 641 via hinge portion 645. The cover hinge portion 645 may be offset from the middle of the oval body 600 so that the cover portion 641 is longer than the base portion 621. A cover coupling mechanism or latch 660 may be provided on cover portion 641 and may be positioned to snap over the outer edge of body portion 621 in the closed condition, as illustrated in FIG. 24.

Figure 20:
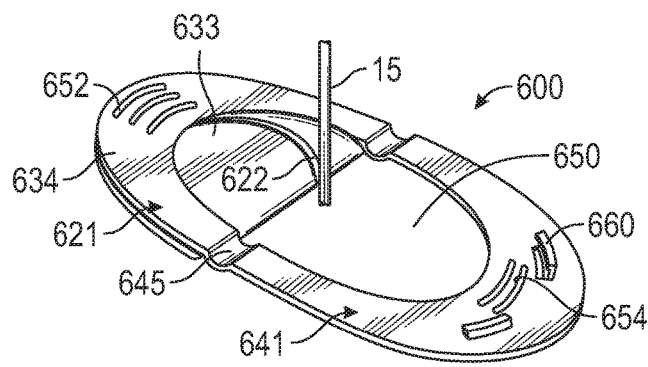
FIG. 20 is a perspective view of an alternate embodiment of the device body of FIGS. 1, 11, and 16 in an open condition.
Figure 21:
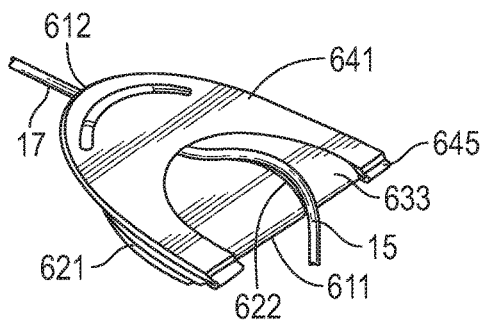
FIG. 21 is a perspective view of the device body of FIG. 20 in a closed condition.
Figure 22:
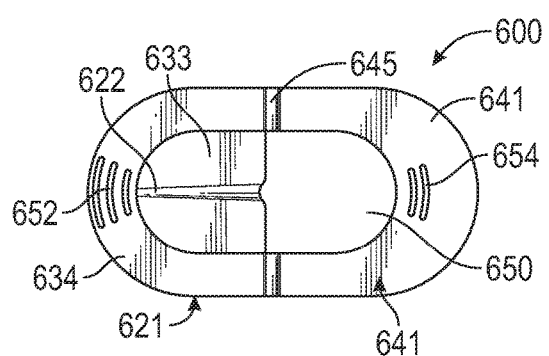
FIG. 22 is a top view of the device body of FIG. 20 in the open condition.
Figure 23:
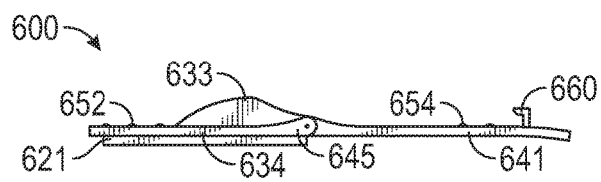
FIG. 23 is a side elevation view of the device body of FIG. 20 in the open condition.

The base portion 621 may include a base plate 634 and a bulbous portion 633. The bulbous portion 633 may be located within an opening in the base plate 634 or may be integrally formed with base plate 634. A base slot or groove 622 may extend from the reception end 611 of base portion 621 along the bulbous portion 633 toward the device distal end 612, the reception end 611 being adjacent the cover hinge 645. In the embodiment illustrated in FIGS. 20-24, the base and cover have opposing gripping features or arc shaped ridges 652 and 654 located on respective outer curved portions of base plate 634 and the cover body 641 which oppose one another in the closed condition of FIGS. 21 and 24. As illustrated in FIG. 20, the central opening 650 of cover portion 640 is engaged over the protruding end portion of wire 15 and base portion 621 is then secured to an underlying region of the patient's skin adjacent the location where wire 15 exits the body, using a similar base (not illustrated) to the base 180 of the first embodiment. Wire 15 is then bent to extend along groove or slot 622 and across the outer end of base plate 634, before closing the cover 641 over the base plate 634 with opening 650 engaging over bulbous portion 633 and the latch 660 engaging over the outer edge of the base plate to releasably lock the cover in the closed position with the wire gripped between ridges 652 and 654, as seen in FIGS. 21 and 24.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

I claim:

1. A wire stabilization device for securing a localization wire to a patient's skin, the wire stabilization device comprising:
   a device body having a reception end for receiving a localization wire adjacent to location that the localization wire exits the patient's skin, a device distal end opposite the reception end, and a device first side opposite a device second side; and
   a device base secured to the device body and having an adhesive portion for adhesive attachment to the patient's skin;
   the device body including:
   a base portion,
   a cover hinge adjoining a first side of the base portion,
   a cover portion adjoining the cover hinge and rotatable about the cover hinge between an open position spaced from the base portion and a closed position extending over the base portion,
   a gripping mechanism between opposing inner surfaces of the base portion and cover portion in the closed position, the gripping mechanism comprising ribs including first and second cover ribs and a first base rib, wherein the gripping mechanism is configured to grip a portion of the localization wire extending between the base portion and the cover portion from the reception end to the device distal end, and
   wherein the first base rib interleaves and extends into a space between the first and second cover ribs when the cover portion is in the closed position, and
   a cover coupling mechanism which releasably holds the cover portion in the closed position;
   wherein the device base comprises a first panel of pliable material having an upper surface, a lower surface including the adhesive portion, and a peripheral edge, and an adhesive joining portion secured between the upper surface of the first panel and the device body, the first panel being of larger peripheral dimensions than the device body and the joining portion, and the first panel having a slot for receiving the localization wire, the slot extending inward from the peripheral edge up to the joining portion and the reception end of the device body; and
   wherein the base portion has a recess at the reception end of the device body aligned with the slot in the first panel of the device base, and
   wherein during use of the stabilization device, the localization wire is bent at a location adjacent to the reception end and runs parallel across the patient's skin and transversely across the ribs of the gripping mechanism by the recess guiding the localization wire across the base portion to the device distal end.

2. The wire stabilization device of claim 1, wherein the cover portion includes a cover body and cover walls extending from the cover body towards the base portion during the closed position, the cover walls being shaped to include a cover entrance slot between the cover portion and base portion at the reception end and a cover exit slot between the cover portion and base portion at the device distal end during the closed position.

3. The wire stabilization device of claim 2, wherein the base portion includes an inwardly extending recess at the reception end which is aligned with the cover entrance slot in the closed position of the cover portion, wherein the inwardly extending recess is configured to receive a portion of the localization wire exiting the patient's skin during attachment of the device base to the patient's skin.

4. The wire stabilization device of claim 1, wherein the base portion includes a tab that extends from a second side of the base portion.

5. The wire stabilization device of claim 1, wherein the base portion includes a first portion joined to the device base, a base hinge adjoining the first portion at the reception end, and a second portion adjoining the base hinge, the second portion rotating about the base hinge between a base open position away from the first portion to a base closed position adjacent the first portion.

6. The wire stabilization device of claim 5, wherein the base portion further includes a body coupling mechanism that holds the second portion in the closed position adjacent the first portion.

7. The wire stabilization device of claim 1, further comprising at least one adhesive member for applying over a portion of a localization wire extending out of the device distal end during securement of the cover portion over the base portion with the localization wire extending between opposing inner faces of the cover portion and base portion after the device base is attached to the patient's skin.

* * * * *